United States Patent [19]
Ling et al.

[11] Patent Number: 6,007,491
[45] Date of Patent: Dec. 28, 1999

[54] CARDIAC OUTPUT MONITOR USING FUZZY LOGIC BLOOD PRESSURE ANALYSIS

[75] Inventors: Jian Ling; Dean Carl Winter; Brian L. Robey, all of San Antonio, Tex.

[73] Assignee: Southwest Research Institute, San Antonio, Tex.

[21] Appl. No.: 09/020,177

[22] Filed: Feb. 6, 1998

[51] Int. Cl.⁶ .................................................. A61N 5/00
[52] U.S. Cl. ........................ 600/481; 128/920; 600/300
[58] Field of Search ................................. 600/481–503, 600/529–538, 300; 128/920–925

[56] References Cited

U.S. PATENT DOCUMENTS

| | | |
|---|---|---|
| 5,390,679 | 2/1995 | Martin .................................... 128/673 |
| 5,685,316 | 11/1997 | Schookin et al. ...................... 128/713 |
| 5,797,850 | 8/1998 | Archibald et al. ..................... 600/494 |

*Primary Examiner*—Cary O'Connor
*Assistant Examiner*—Michael Astorino
*Attorney, Agent, or Firm*—Baker & Botts, L.L.P.

[57] ABSTRACT

A method of monitoring cardiac output. The method uses a blood pressure waveform as input. The waveform is digitized and various blood pressure features are extracted. The features are used as inputs to a fuzzy logic model, where each input is fuzzified by determining its degree of confidence as a member of one or more fuzzy membership regions. A rule base is applied to the defuzzified inputs to obtain a fuzzy stroke volume index. This output is defuzzied and used to calculate cardiac output.

20 Claims, 4 Drawing Sheets

6,007,491

CARDIAC OUTPUT MONITOR USING FUZZY LOGIC BLOOD PRESSURE ANALYSIS

TECHNICAL FIELD OF THE INVENTION

This invention relates to medical monitoring instruments, and more particularly to a method of monitoring cardiac output.

BACKGROUND OF THE INVENTION

Cardiac output is the measure of average blood flow through the heart. It is the product of the heart rate times the stroke volume. For a healthy adult in rest, a normal cardiac output is about 5 liters per minute. A healthy human body attempts to maintain a normal cardiac output by increasing or decreasing the heart rate or stroke volume. If the body cannot adequately compensate heart rate or stroke volume, adverse physiological conditions occur.

The measurement of cardiac output is an important part of health care. One method of measuring cardiac output is based on the principle of thermodilution. A catheter is inserted into a peripheral vein and the catheter tip is threaded into the pulmonary artery. Cold saline is injected through the catheter into the blood approximately three inches from the catheter tip. As the blood carries the saline past the catheter tip, a thermistor detects the decrease in temperature of the blood/saline mix. The measured temperature dilution is used to estimate cardiac output.

Another method of measuring cardiac output is based on the arterial blood pressure waveform. An advantage of this method is that the waveform can be obtained from non-invasive or minimally invasive devices.

The principle of obtaining cardiac output from blood pressure is analogous to the principle of electrical circuit analysis. Cardiac output can be derived from blood pressure if cardiovascular impedance is known, in a manner analogous to deriving electrical current from voltage if circuit impedance is known.

Various approaches have been used to provide a model for obtaining cardiac output from blood pressure. A well-known electrical analog model is known as the Windkessal model, developed in the 1930's. Linear and non-linear variations of this model have been developed.

More recently developed blood pressure models depart from analog models. For example, one approach uses pattern recognition to obtain a continuous cardiac output measurement from arterial pressure waveforms. U.S. Pat. No. 5,390,679, to Martin, entitled "Continuous Cardiac Output derived from the Arterial Pressure Waveform Using Pattern Recognition", describes this approach.

SUMMARY OF THE INVENTION

One aspect of the invention is a cardiac output monitoring system. An analog-to-digital converter receives a blood pressure waveform and converts the waveform to blood pressure waveform data. A digital signal processor then processes the blood pressure waveform data so as to obtain blood pressure feature data, such as data representing systolic area and vascular resistance. The feature data is input to a fuzzy logic processor, which applies a set of fuzzy logic rules to the feature data, and obtains a stroke volume index. The stroke volume index is multiplied times heart rate and the patient's body surface area to provide the cardiac output.

An advantage of the cardiac output monitor is that it provides a real-time continuous reading of cardiac output. The output is updated in response to the continuous blood pressure waveform.

Furthermore, the monitor can be used with a minimum of intervention by the health care provider. It can use blood pressure readings from conventional blood pressure monitoring devices that may already be in use with a patient, thereby eliminating the need for additional apparatus. It is convenient and cost effective.

DETAILED DESCRIPTION OF THE INVENTION

Figure 1:
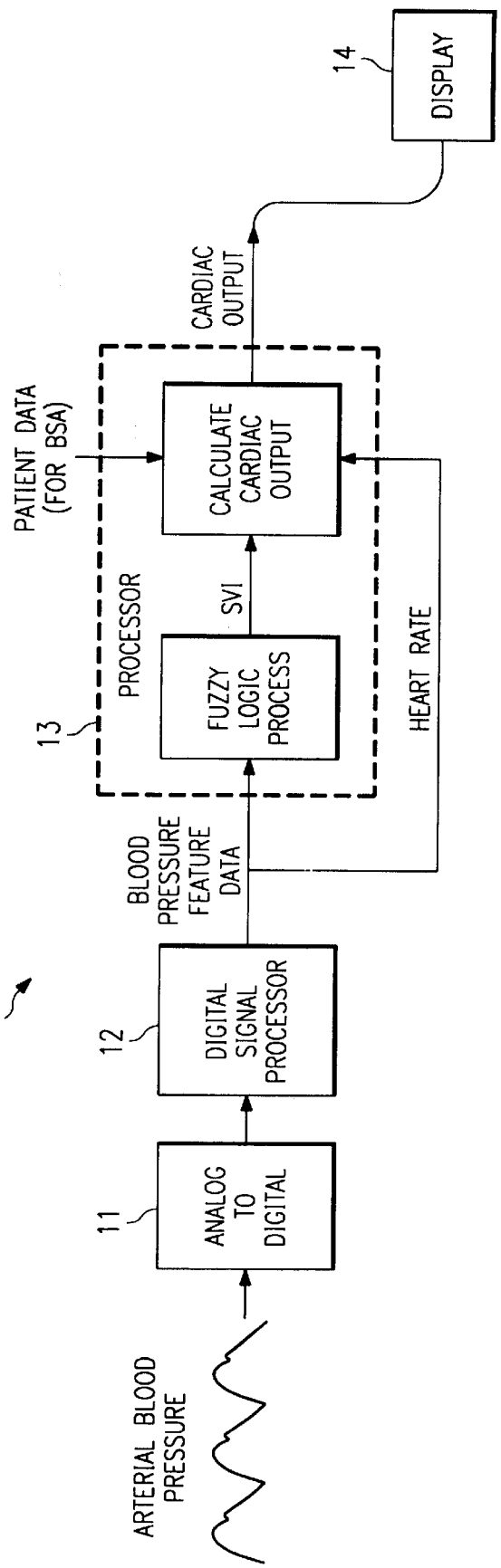
FIG. 1 is a block diagram of a cardiac output monitor in accordance with the invention.
Figure 2:
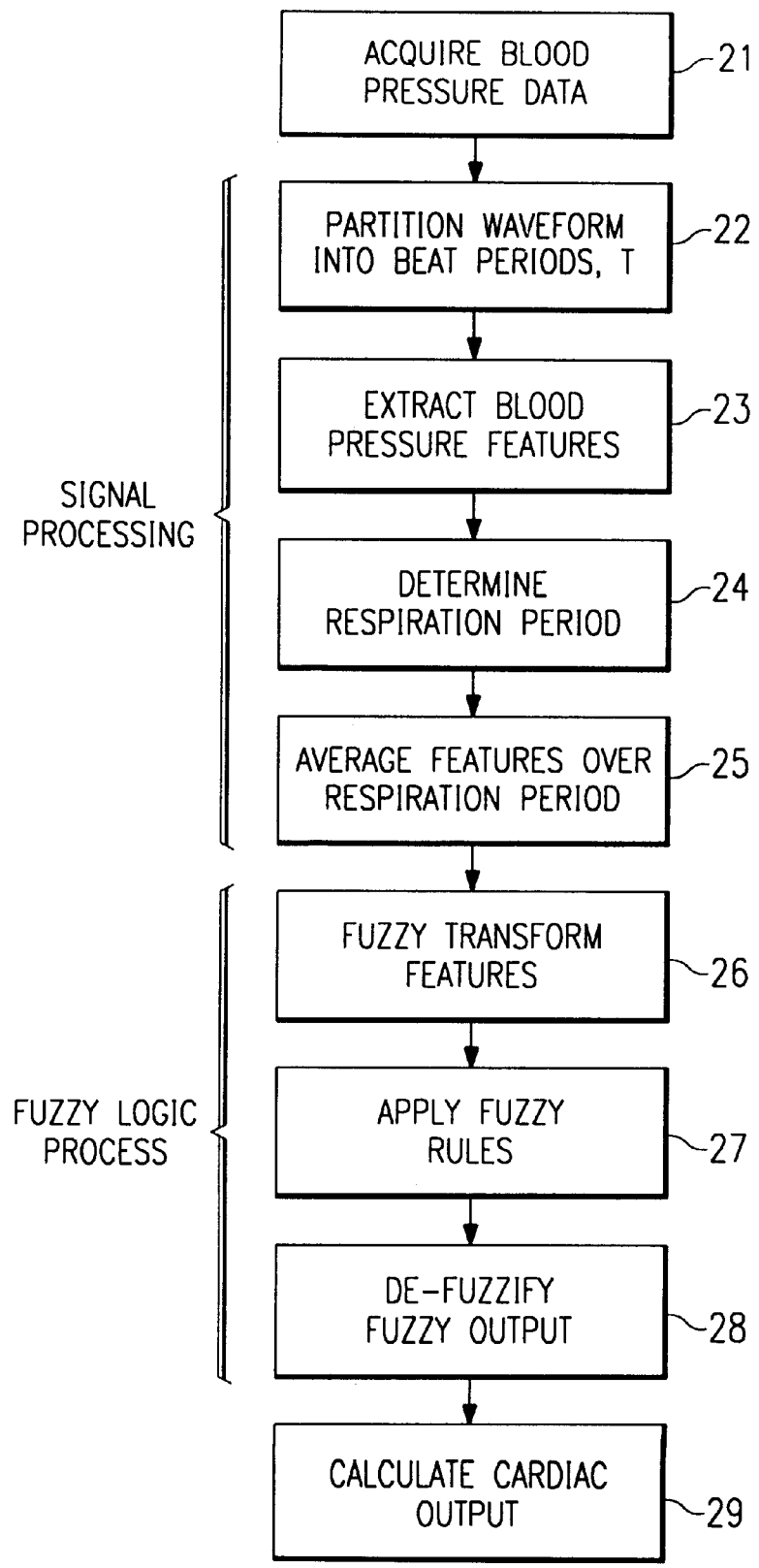
FIG. 2 illustrates the process performed by the monitor of FIG. 1.

FIG. 1 is a block diagram of a cardiac output monitor 10 in accordance with the invention. FIG. 2 illustrates a method of monitoring cardiac output in accordance with the invention. The method of FIG. 2 may be performed with the monitor 10 of FIG. 1, or with a single processor appropriately programmed to perform the method.

Monitor 10 can be used as an add-on to an existing arterial blood pressure monitoring system or as a stand-alone system. In the case where monitor 10 is added to an existing system, the input data might already be in digital form, eliminating the need for analog-to-digital converter 11.

The input to monitor 10 is an analog waveform representing arterial blood pressure of the subject patient. This input is typically available at the patient's bedside in an operating room, intensive care unit, or other critical care setting. The waveform can be obtained directly from a catheter placed in the aortic or radial artery or from some other blood pressure sensing device. Monitor 10 could be easily adapted for a femoral arterial input.

Cardiac output monitor 10 is comprised of an analog-to-digital converter 11, digital signal processor 12, general purpose processor 13, and display 14. As explained below, monitor 10 uses blood pressure features, which are extracted by digital signal processor 12, as input to a fuzzy logic model stored in memory of processor 13. Digital signal processor 12 also determines a heart rate value. Processor 13 uses the fuzzy logic model to determine a stroke volume index value. The product of the stroke volume index, body surface area, and heart rate is the cardiac output value. These values are continuously updated in response to the input waveform and displayed on a display 14.

Referring to both FIGS. 1 and 2, in Step 21, an analog arterial blood pressure waveform is input to analog-to-digital converter 11 where it is converted to a digital data signal.

In Steps 22–25, the digital signal provided by analog-to-digital converter 11 is processed by digital signal processor 12. Digital signal processor 12 may be any one of the various integrated circuits especially developed for executing digital signal processing algorithms and is assumed to have associated memory in which appropriate programming is stored.

Figure 3:
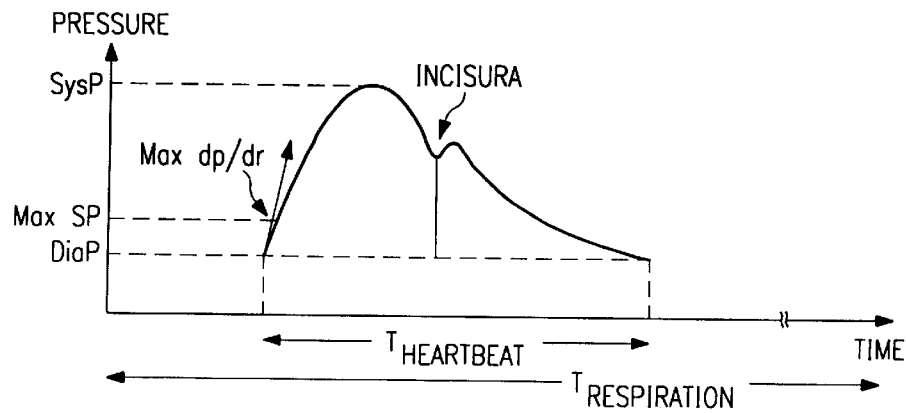
FIG. 3 illustrates the blood pressure waveform input to the monitor of FIG. 1.

FIG. 3 illustrates the blood pressure waveform and several blood pressure features. The systolic pressure, SysP, is the maximum pressure on the walls of the arteries with each beat of the heart. The diastolic pressure, DiaP, is the minimum pressure on the walls of the arteries.

Referring to both FIGS. 2 and 3, Step 22 of the digital signal processing is partitioning the waveform into beat-by-beat periods, T. Each period begins and ends at a "valley" of the waveform, that is, at the points of the waveform where it is at the diastolic pressure.

Step 23 is extracting specified waveform features for each period, T. As explained below in connection with FIGS. 4–6, these features depend on whether the input is aortic or radial arterial blood pressure.

Step 24 is determining the respiration period, $T_{respiration}$. This may be accomplished by detecting fluctuations of the systolic pressure and diastolic pressure.

Step 25 is averaging the extracted features within one respiration period so as to cancel respiration artifacts on the blood pressure waveform. Step 25 is performed for each feature, and as a result of Step 25, for each feature, an average feature value per respiration period is obtained.

Figure 4:
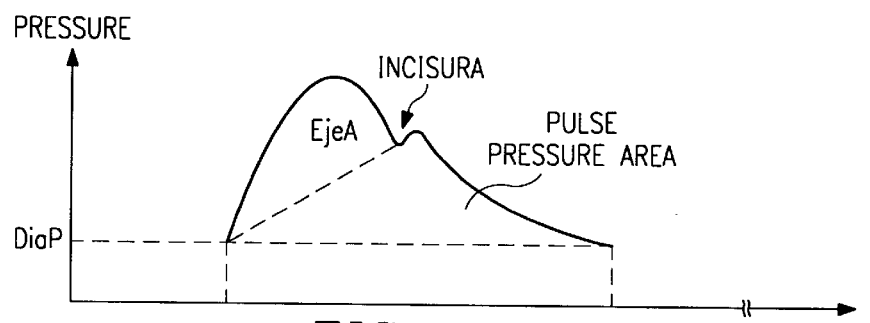
FIGS. 4, 5 and 6 illustrate the EjeA, SysA, and Width features, respectively.
Figure 5:
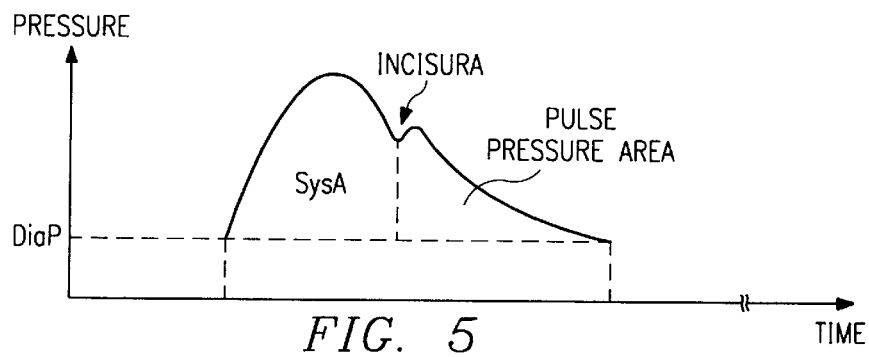
Figure 6:
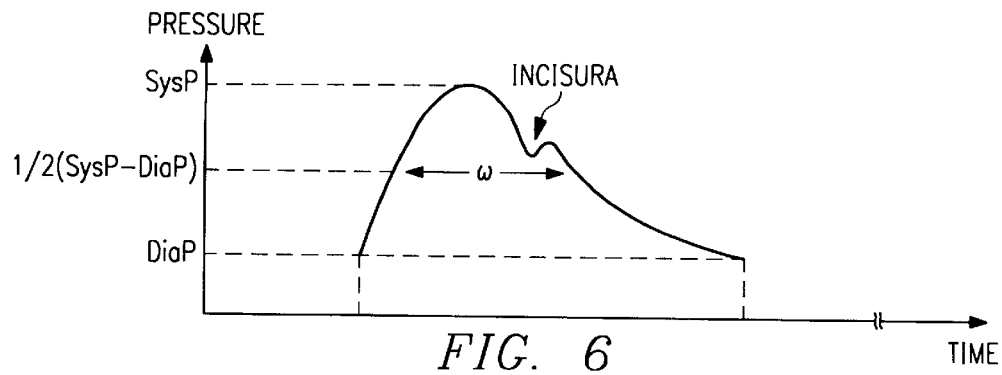

FIGS. 4–6 are additional illustrations of one beat of an input waveform and of features extracted during signal processing. When the input waveform represents aortic arterial pressure, the following features are extracted in Step 23:

| symbol | definition | units |
| --- | --- | --- |
| SysP | systolic pressure | mmHg |
| DiaP | diastolic pressure | mmHg |
| EjeA | eject area | mmHg × seconds |
| VRI | vascular resistance index | ms |
| WEI | Wesseling index | |
| HR | heart rate | beats/minute |

As used herein, the "pulse pressure area" is the area for one period, T, under the blood pressure curve not including the DC portion of the curve (the portion under DiaP). As illustrated in FIG. 4, the eject area, EjeA, is the pulse pressure area, truncated by a straight line from the first diastolic point to the incisura.

The vascular resistance index, VRI, is calculated as follows:

$$VRI = 1000 \times \frac{\text{Max}SP}{\text{Max } dp/dt}$$

where MaxSP is the pressure at the point where dp/dt (pressure differentiated with respect to time) is a maximum. The Wesseling index, WEI, is calculated as follows:

WEI=(163+HR−0.48×MAP)×SysA, where MAP is mean arterial pressure and SysA is the systolic area. SysA is calculated as the pulse pressure area prior to the time of the incisura, as illustrated in FIG. 5. In other words, SysA is the integration of the pulse pressure during the systolic period.

The heart rate, HR, is estimated as follows:

HR=60,000/T.

When the input waveform represents radial arterial pressure, the following features are extracted in Step 23:

| symbol | definition | units |
| --- | --- | --- |
| DiaP | diastolic pressure | mmHg |
| SysA | systolic area | mmHg × seconds |
| VRI | vascular resistance index | ms |
| WEI | Wesseling index | |
| Width | width at half amplitude | ms |
| HR | heart rate | beats/minute |

The systolic area, SysA, is calculated as described above in connection with FIG. 5. The Width feature is the pulse width at half amplitude, where half amplitude is calculated as follows:

½×(SysP−DiaP), as illustrated in FIG. 6.

For both aortic and radial blood pressure waveforms, the systolic area, SysA, and vascular resistance index, VRI, are important features for determining the stroke volume index. SysA is related to the force that drives the blood flow, whereas VRI is related to the resistance of the blood flow. The other features listed above provide additional data that qualifies SysA and VRI.

Figure 7:
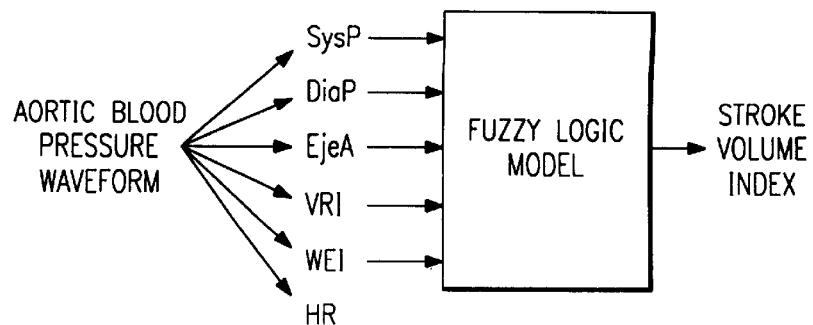
FIG. 7 illustrates the fuzzy logic process when the input waveform represents aortic blood pressure.
Figure 8:
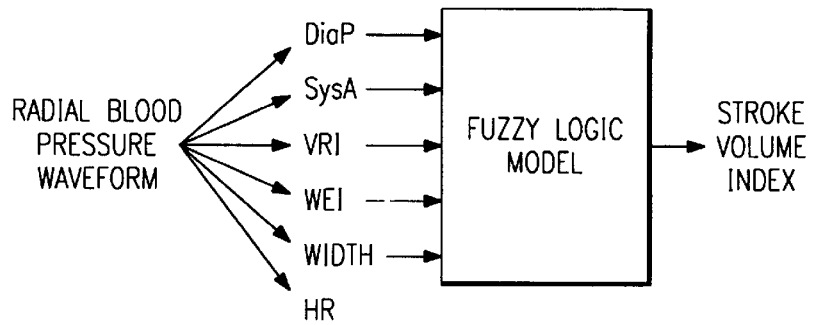
FIG. 8 illustrates the fuzzy logic process when the input waveform represents aortic radial blood pressure.

FIGS. 7 and 8 illustrate the data received by processor 13 from digital signal processor 12, when the inputs are aortic and radial blood pressure waveforms, respectively. Referring again to FIG. 1 as well as to FIGS. 7 and 8, processor 13 applies a fuzzy logic process to the feature data to obtain a fuzzy stroke volume index (SVI) value. Processor 13 may be any type of general purpose or dedicated processor having memory for storing appropriate programming and for performing calculations.

To develop the fuzzy logic process, the input feature variables and the output variable, SVI, are partitioned into fuzzy regions. For each variable, the partitioning is in accordance with a membership function and the results are stored in memory of processor 13.

Figure 9:
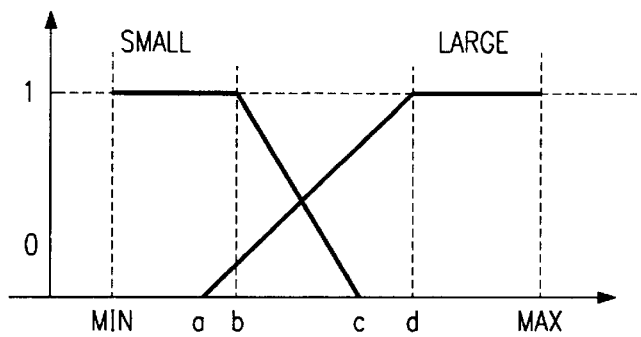
FIG. 9 illustrates a membership function for blood pressure feature variables that are to be input to the fuzzy logic process.
Figure 10:
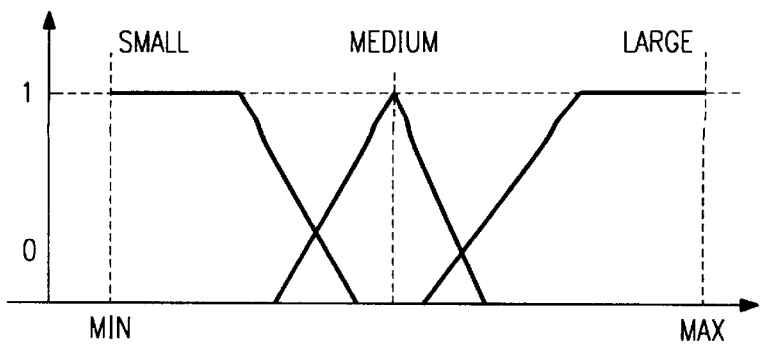
FIG. 10 illustrates a membership function for the stroke volume index variable that is output from the fuzzy logic process.

FIGS. 9 and 10 illustrate the partitioning and membership functions for the input feature variables and the output variable, SVI, respectively. In the example of this description, the input features are partitioned into small and large regions. The stroke volume index is partitioned into small, medium, and large regions. However, any number of partitions can be used.

In the example of this description, the membership functions are ramp functions, but other membership functions could be used. For example, the membership functions could be curves or triangular functions. In any event, the "steepness" of the function defines the "fuzziness" of the variable. The points on the function indicate the degree of confidence that any variable belongs to a fuzzy region. A variable may belong to more than one fuzzy region, with different degrees of confidence.

During development of the fuzzy logic process, various techniques may be used to optimize the function parameters, such as the a,b,c,d parameters in FIG. 9. For example, a genetic algorithm could be used where the membership function is evaluated with respect to experimental data, and parameters with the improved fitness are selected for the next membership function. This process is repeated until the developer is satisfied that an optimal membership function has been generated. This membership function is then stored in processor 13 as described above.

Referring again to FIGS. 1 and 2, in Step 26, processor 13 assigns the input features to one or more membership functions. In Step 27, processor 13 applies a set of rules to estimate the SVI output. This set of rules, e.g., the fuzzy rule base, defines relationships between feature inputs and a SVI output. Each input feature belongs to one or more of the membership regions (fuzzy sets). The value of the input determines its degree of confidence as a member of the region. Thus, for example, referring to FIG. 9, if a feature value were between min and a, it would have a degree of confidence rating of 1.0.

When the input is an aortic blood pressure waveform, an example of a suitable rule base is one having the following rules:

1) IF SysP is small, DiaP is small, EjeA is small, VRI is small, WEI is small, THEN SVI is small.
2) IF SysP is small, DiaP is small, EjeA is small, VRI is large, WEI is small, THEN SVI is small.
3) IF SysP is small, DiaP is small, EjeA is large, VRI is small, WEI is small, THEN SVI is medium.
4) IF SysP is large, DiaP is large, EjeA is small, VRI is large, WEI is small, THEN SVI is medium.
5) IF SysP is large, DiaP is large, EjeA is small, VRI is small, WEI is large, THEN SVI is medium.
6) IF SysP is large, DiaP is large, EjeA is small, VRI is small, WEI is large, THEN SVI is medium.
7) IF SysP is large, DiaP is large, EjeA is small, VRI is small, WEI is small, THEN SVI is medium.
8) IF SysP is large, DiaP is large, EjeA is large, VRI is large, WEI is large, THEN SVI is medium.
9) IF SysP is small, DiaP is small, EjeA is small, VRI is small, WEI is large, THEN SVI is medium.
10) IF SysP is large, DiaP is small, EjeA is small, VRI is small, WEI is small, THEN SVI is medium.
11) IF SysP is large, DiaP is small, EjeA is large, VRI is small, WEI is large, THEN SVI is large.
12) IF SysP is large, DiaP is large, EjeA is large, VRI is small, WEI is large, THEN SVI is large.

If the input is a radial blood pressure waveform, an example of a suitable rule base is one having the following rules:

1) IF DiaP is small, SysA is small, VRI is large, WEI is small, Width is large, THEN SVI is small.
2) IF DiaP is small, SysA is small, VRI is large, WEI is small, Width is small, THEN SVI is small.
3) IF DiaP is large, SysA is large, VRI is small, WEI is large, Width is small, THEN SVI is medium.
4) IF DiaP is small, SysA is small, VRI is small, WEI is small, Width is large, THEN SVI is medium.
5) IF DiaP is large, SysA is large, VRI is large, WEI is large, Width is small, THEN SVI is medium.
6) IF DiaP is large, SysA is small, VRI is large, WEI is large, Width is small, THEN SVI is medium.
7) IF DiaP is small, SysA is small, VRI is small, WEI is small, Width is small, THEN SVI is medium.
8) IF DiaP is large, SysA is small, VRI is large, WEI is small, Width is large, THEN SVI is medium.
9) IF DiaP is small, SysA is small, VRI is large, WEI is large, Width is large, THEN SVI is medium.
10) IF DiaP is small, SysA is large, VRI is large, WEI is large, Width is large, THEN SVI is medium.
11) IF DiaP is large, SysA is large, VRI is large, WEI is large, Width is large, THEN SVI is medium.
12) IF DiaP is large, SysA is small, VRI is small, WEI is large, Width is small, THEN SVI is medium.
13) IF DiaP is small, SysA is large, VRI is small, WEI is large, Width is small, THEN SVI is medium.
14) IF DiaP is large, SysA is large, VRI is small, WEI is large, Width is large, THEN SVI is medium.
15) IF DiaP is small, SysA is large, VRI is small, WEI is large, Width is small, THEN SVI is large.
16) IF DiaP is small, SysA is small, VRI is small, WEI is large, Width is small, THEN SVI is large.

The general pattern of each rule base adheres to the following relationships between SysA, VRI, and SVI:
If SysA is small and VRI is large, then SVI is small.
If SysA is large and VRI is small, then SVI is large.
If SysA is small and VRI is small, then SVI is medium.
If SysA is large and VRI is large, then SVI is medium.

These generalizations are consistent with the physiology of blood flow.

Appropriate rules may be synthesized from experimental data by techniques known in the field of fuzzy logic modeling. To develop a rule base, each input-output pair of variables serves as a candidate rule. The degree of confidence of each rule is calculated based on the degrees of confidence of the input and output variables. Rules with the same "if" and "then" parts are combined. Rules with the same "if" parts but different "then" parts are compared and evaluated on the basis of their degrees of confidence.

In Step 28, after applying the fuzzy rules, processor 13 "defuzzifies" the output of the fuzzy rule base. The outputs of each rule are integrated to obtain a current stroke volume index value. This defuzzification process may use various mathematical techniques known in the art of fuzzy logic. Because of the calculations used in extracting the feature data, the stroke volume output is an index value.

Finally, in Step 29, the cardiac output is determined by multiplying the patient's heart rate times the stroke volume index and the patient's body surface area. The body surface area can be estimated from data such as the height and weight of the patient.

The above-described process operates in real-time, continuously updating the cardiac output in response to the input waveform. Where the input features are averaged over each respiration period, a new cardiac output value is provided for every respiration period.

OTHER EMBODIMENTS

Although the present invention has been described in detail, it should be understood that various changes, substitutions, and alterations can be made hereto without departing from the spirit and scope of the invention as defined by the appended claims.

What is claimed is:

1. A cardiac output monitor, comprising:
   an analog to digital converter for receiving an arterial blood pressure waveform and converting said waveform to blood pressure waveform data;
   a digital signal processor for processing said blood pressure waveform data so as to obtain blood pressure feature data; and
   a fuzzy logic processor programmed to perform a fuzzy logic process on said feature data, using a set of fuzzy logic rules, thereby obtaining stroke volume data.

2. The monitor of claim 1, wherein said blood pressure waveform is an aortic blood pressure waveform.

3. The monitor of claim 1, wherein said blood pressure waveform is a radial blood pressure waveform.

4. The monitor of claim 1, wherein said blood pressure waveform is a femoral blood pressure waveform.

5. The monitor of claim 1, wherein said digital signal processor is programmed to extract a systolic area and a vascular reference index feature.

6. The monitor of claim 5, wherein said digital signal processor is programmed to compensate said systolic area feature by heart rate and mean arterial pressure.

7. The monitor of claim 1, wherein said rules relate a systolic area feature and a vascular resistance index feature to said stroke volume index.

8. The monitor of claim 1, wherein said digital signal processor is programmed to calculate a heart rate value from said blood pressure waveform data.

9. The monitor of claim 1, wherein said digital signal processor is programmed to calculate a respiration period, and a heartbeat period, and to average said features for a number of heartbeat periods within a respiration period.

10. A method of monitoring cardiac output, comprising the steps of:

acquiring arterial blood pressure waveform data;

processing said blood pressure waveform data so as to obtain blood pressure feature data; and applying a fuzzy logic process, using fuzzy logic rules, to said feature data, thereby obtaining stroke volume data.

11. The method of claim 10, wherein said blood pressure waveform is an aortic blood pressure waveform.

12. The method of claim 10, wherein said blood pressure waveform is a radial blood pressure waveform.

13. The method of claim 10, wherein said blood pressure waveform is a femoral blood pressure waveform.

14. The method of claim 10, wherein said feature data comprises a systolic area feature and a vascular reference index feature.

15. The method of claim 14, wherein said systolic area feature is compensated by heart rate and mean arterial pressure.

16. The monitor of claim 10, wherein said rules relate a systolic area feature and a vascular resistance index feature to said stroke volume index.

17. The monitor of claim 10, further comprising the step of processing said blood pressure waveform data to extract a heart rate value.

18. The monitor of claim 10, further comprising the steps of using said blood pressure waveform data to calculate a respiration period and a heartbeat period, and of averaging said features for a number of heartbeat periods within a respiration period.

19. A method of monitoring cardiac output, comprising the steps of:

acquiring arterial blood pressure waveform data;

processing said blood pressure waveform data so as to obtain blood pressure feature data, said blood pressure feature data comprising at least a measure of systolic area and a measure of vascular resistance; and applying a set of fuzzy logic rules to said feature data, thereby obtaining stroke volume data.

20. The method of claim 19, wherein said feature data is calculated such that such stroke volume data is an index value.

* * * * *